United States Patent [19]

Magee

[11] 4,110,443

[45] Aug. 29, 1978

[54] INSECTICIDAL O,S-DIHYDROCARBYL-N-HALOACYL-PHOSPHOROAMIDOTHIOATES AND S,S-DIHYDROCARBYL-N-HALOACYL-PHOSPHOROAMIDODITHIOATES

[75] Inventor: Philip S. Magee, Ignacio, Calif.

[73] Assignee: Chevron Research Company, San Francisco, Calif.

[21] Appl. No.: 805,494

[22] Filed: Jun. 10, 1977

Related U.S. Application Data

[60] Division of Ser. No. 317,316, Dec. 21, 1972, Pat. No. 4,049,679, which is a continuation-in-part of Ser. No. 13,846, Feb. 24, 1972, Pat. No. 3,716,600, which is a continuation-in-part of Ser. No. 810,383, Mar. 25, 1969, abandoned.

[51] Int. Cl.$^2$ ................................................ A01N 9/36

[52] U.S. Cl. ..................................... 424/212; 424/220; 260/941

[58] Field of Search .................... 424/219, 220, 212

[56] References Cited

U.S. PATENT DOCUMENTS

| | | | |
|---|---|---|---|
| 3,201,446 | 8/1965 | Tolkmith | 260/959 |
| 3,309,266 | 3/1967 | Magee | 424/220 |

*Primary Examiner*—V. D. Turner
*Attorney, Agent, or Firm*—Dix A. Newell; T. G. DeJonghe; Raymond Owyang

[57] ABSTRACT

O,S-dihydrocarbylphosphoroamidothioates and S,S-dihydrocarbylphosphoroamidothioates have a high degree of insecticidal activity with relatively low mammalian toxicity.

16 Claims, No Drawings

INSECTICIDAL O,S-DIHYDROCARBYL-N-HALOACYLPHOSPHOROAMIDOTHIOATES AND S,S-DIHYDROCARBYL-N-HALOACYLPHOSPHOROAMIDODITHIOATES

CROSS-REFERENCE TO RELATED APPLICATIONS

This application is a division of application Ser. No. 317,316, filed Dec. 21, 1972, now U.S. Pat. No. 4,049,679, which, in turn, is a continuation-in-part of U.S. Ser. No. 13,846, filed Feb. 24, 1972, now U.S. Pat. No. 3,716,600 which, in turn, is a continuation-in-part of U.S. Ser. No. 810,383, filed Mar. 25, 1969, now abandoned.

DESCRIPTION OF THE PRIOR ART

U.S. Pat. No.. 3,309,266 teaches that O-alkyl-S-alkyl phosphoroamidothioates are insecticidal. U.S. Pat. No. 3,649,723 teaches that O-alkyl-S-unsaturated hydrocarbylphosphoroamidothioates are insecticidal. U.S. Pat. No. 3,201,446 teaches that O,O-diethyl-N-trichloroacetylphoshoroamidothioate [N-(di-ethoxyphosphinothioyl)-2,2,2-trichloroacetamide] is useful as an insecticide. Russian Pat. No. 253,483, issued on Sept. 30, 1969 to G. V. Protopopova et al., discloses the use of O,S-dialkyl-N-alkylthiocarbonylphosphoroamidothioates, e.g.,

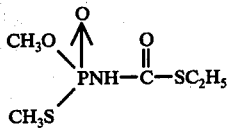

as insecticides. L. Almasi et al., Chem. Ber. 100 2626 (1967) and Chem. Ber. 99, 3293 (1966), disclose O-ethyl-S-methyl-N-benzoylphoshoroamidothioate, O-ethyl-S-methyl-N-p-chlorobenzoylphosphoroamidothioate and O-ethyl-S-methyl-N-p-methylbenzoylphosphoromidothioate.

DESCRIPTION OF THE INVENTION

The compounds of this invention are represented by the formula (I):

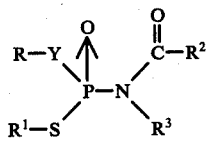

wherein R and $R^1$ individually are alkyl, alkenyl or alkynyl of up to 6 carbon atoms, $R^2$ is haloalkyl of 1 to 18 carbon atoms and 1 to 4 fluorine, chlorine or bromine atoms, $R^3$ is hydrogen or alkyl of 1 to 6 carbon atoms and Y is oxygen or sulfur.

Representative alkyl groups which R, $R^1$ and $R^3$ may represent include methyl, ethyl, propyl, isopropyl, butyl, isobutyl, t-butyl, pentyl, sec-pentyl and hexyl. Representative alkenyl groups which R and $R^1$ may representative include allyl, 2-butenyl, isobutenyl, 3-pentenyl, 2-hexenyl, etc. Representative alkynyl of 3 to 6 carbon atoms which R and $R^1$ may represent include 2-propynyl, 2-butynyl, 3-hexynyl, etc. Preferred R and $R^1$ groups are alkyl of 1 to 3 carbon atoms, especially methyl. The preferred $R^3$ group is hydrogen.

Representative $R^2$ groups include in fluoromethyl, chloromethyl, bromomethyl, difluoromethyl, dichloromethyl, 2-fluoroethyl, 2-chloroethyl, 2-bromoethyl, 2,2-difluoroethyl, 1,2-dichloroethyl, 2,2-dichloroethyl, 2-bromo-2-chloroethyl, 1,1,2,2-tetrachloroethyl, 1,2,2,2-tetrachloroethyl, pentachloroethyl, 1,2-dibromoethyl, 3-fluoropropyl, 3-chloropropyl, 3-bromopropyl, 4-chlorobutyl, 5-bromopentyl, 2,4,6-trichlorohexyl, 3,5-dibromopentyl, 6-chlorohexyl, 7-chloroheptyl, 3-chloro-5,6-dibromoethyl, 11-chloroundecyl, 11-bromododecyl, 15-chloropentadecyl, 8,9-dichloropentadecyl, 17-bromoheptadecyl. Preferred $R^2$ groups are haloalkyl of 1 to 11 carbon atoms and 1 to 2 chlorine or bromine atoms. The most preferred $R^2$ groups are haloalkyl of 1 to 3 carbon atoms and 1 to 2 chlorine or bromine atoms, especially halomethyl.

Representative N-haloalkanoylphosphoroamidothioate compounds of formula (I) are: O-methyl-S-allyl-N-fluoroacetylphosphoroamidothioate, O-methyl-S-methyl-N-chloroacetylphosphoroamidothioate, O-allyl-S-allyl-N-dibromoacetylphoshoroamidothioate, O-allyl-S-ethyl-N-difluoroacetylphosphoroamidothioate, O-methyl-S-methyl-N-methyl-N-trifluoroacetylphosphoroamidothioate, O-methyl-S-methyl-N-tribromoacetylphosphoroamidothioate, O-propyl-S-isopropyl-N-isopropyl-N-2,2-difluoropropionylphosphoroamidothioate, O-methyl-S-methyl-N-2,3-dichloropropionylphosphoroamidothioate, O-methyl-S-methyl-N-3,3-dibromopropionylphosphoroamidothioate, O-methyl-S-butyl-N-2,3,3,3-tetrachloropropionylphosphoroamidothioate, O-butyl-S-butyl-N-2,2,3,3-tetrachloropropionylphosphoroamidothioate, O-methyl-S-methyl-N-3,4-dichlorobutyrylphosphoroamidothioate, O-propargyl-S-methyl-N-hexyl-N-4-bromobutyrylphosphoroamidothioate, O-methyl-S-methyl-N-5-chloropentanoylphosphoroamidothioate, O-methyl-S-methyl-N-6-fluorohexanoylphosphoroamidothioate, O-methyl-S-methyl-N-7-bromoheptanoylphosphoroamidothioate, O-pentyl-S-methyl-N-7,7-dibromoheptanoylphosphoroamidothioate, O-methyl-S-methyl-N-2,6-dibromooctanoylphoshoroamidothioate, O-methyl-S-methyl-N-8-chlorooctanoylphosphoroamidothioate, O-methyl-S-hexyl-N-10-chlorodecanoylphosphoroamidothioate, O-methyl-S-methyl-N-13-bromotridecanoylphosphoroamidothioate and O-methyl-S-methyl-N-19-chlorononedecanoylphosphoroamidothioate.

Representative N-haloalkanoylphosphoroamidodithioate compounds of formula (I) are: S-methyl-S-allyl-N-fluoroacetylphosphoroamidodithioate, S-methyl-S-methyl-N-chloroacetylphosphoroamidodithioate, S-methyl-S-methyl-N-dibromoacetylphosphoroamidodithioate, S-ethyl-S-ethyl-N-difluoroacetylphosphoroamidodithioate, S-allyl-S-allyl-N-trifluoroacetylphosphoroamidodithioate, S-methyl-S-methyl-N-methyl-N-trichloroacetylphosphoroamidodithioate, S-allyl-S-methyl-N-tribromoacetylphosphoroamidodithioate, S-propyl-S-isopropyl-N-isopropyl-N-2,2-difluoropropionylphosphoroamidodithioate, S-methyl-S-methyl-N-2,3-dichloropropionylphosphoroamidodithioate, S-propargyl-S-allyl-N-3,3-dibromopropionylphosphoroamidodithioate, S-methyl-S-butyl-N-2,3,3,3-tetrachloropropionylphoshoroamidodithioate, S-butyl-S-butyl-N-2,2,3,3-tetrachloropropionylphosphoroamidodithioate, S-methyl-S-methyl-N-3,4- dichlorobutyrylphosphoroamidodithioate, S-methyl-S-methyl-N-4-bromobutyrylphosphoroamidodithioate, S-methyl-S-methyl-N-5-chloropentanoylphosphoroamidodithioate, S-methyl-S-methyl-N-6-fluorohexanoylphosphoroamidodithioate, S-methyl-S-methyl-N-bromoheptanoylphosphoroamidodithioate, S-pentyl-S-methyl-N-hexyl-N-7,7-dibromoheptanoylphosphoroamidodithioate, S-methyl-S-methyl-N-2,6-dibromooctanoylphosphoroamidodithioate, S-methyl-S-methyl-N-8-chlorooctanoylphosphoroamidodithioate, S-methyl-S-hexyl-N-10-chlorodecanoylphosphoroamidodithioate, S-methyl-S-methyl-N-13-bromotridecanoylphosphoroamidodithioate and S-methyl-S-methyl-N-19-chlorononedecanoylphosphoroamidodithioate.

The preferred compounds of formula (I) are O,S-dialkyl-N-haloalkanoylphosphoroamidothioates where R and $R^1$ are alkyl of 1 to 3 carbon atoms, $R^2$ is haloalkyl of 1 to 3 carbon atoms and 1 to 2 fluorine, chlorine or bromine atoms, and $R^3$ is hydrogen.

The compounds of formula (I) may be prepared by acylating an appropriate O-hydrocarbyl-S-hydrocarbylphosphoroamidothioate or S-hydrocarbyl-S-hydrocarbylphosphoroamidodithioate. O-alkyl-S-alkylphosphoroamidothioates and their preparation are disclosed in U.S. Pat. No. 3,309,266. O-alkyl-S-unsaturated hydrocarbyl phosphoroamidothioates and their preparation are disclosed in U.S. Pat. No. 3,649,723.

Conventional acylating agents, such as haloalkanoylhalides, haloketenes and haloalkanoic acid anhydrides and conventional acylating conditions may be used in this reaction. Haloalkanoyl chlorides are preferred acylating agents.

This acylation reaction (illustrated with a haloalkanoylchloride as the acylating agent) may be represented by the following equation:

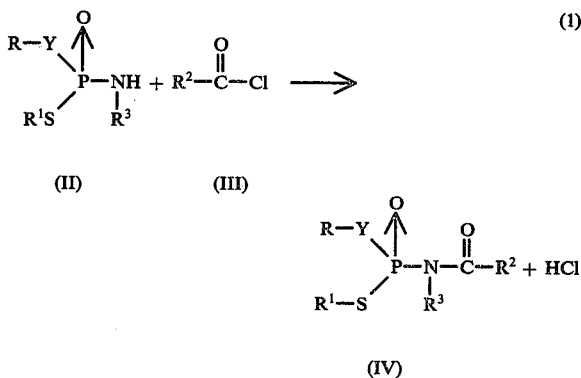

where R, $R^1$, $R^2$, $R^3$ and Y have the same significance as previously defined. This acylation will usually be carried out at about 0° to 60° C. in the presence of solvents such as methylene chloride, chloroform, tetrahydrofuran and benzene. Pressure is not critical in this reaction. For convenience, atmospheric or autogenous pressure will be used. Under normal conditions, stoichiometric proportions or a slight deficiency of the acylating agent will be used. The acylation will usually take 2 to 24 hours to reach completion. The reaction product may be purified by conventional extraction and recrystallization techniques.

The N-haloalkanoylphosphoroamidothioates of this invention may also be prepared by acylating an appropriate O,O-hydrocarbyl phosphoroamidothionate and then isomerizing the resulting N-haloalkanoylphosphoroamidothionate with an alkylating agent to produce the O-hydrocarbyl-S-hydrocarbyl-N-haloakanoylphosphoroamidothionate. This reaction scheme is represented (using a haloalkanoyl chloride as the alkylating agent) by the following equation:

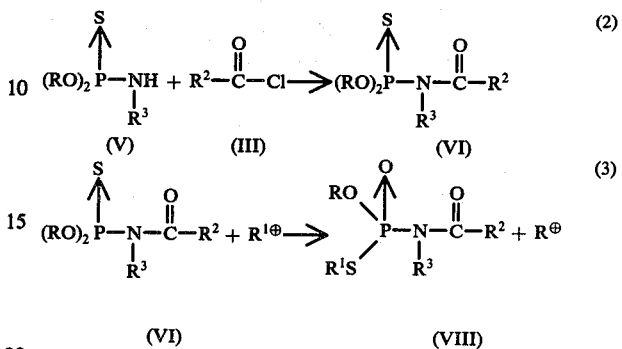

wherein $R^{1\oplus}$ represents an alkylating agent corresponding to $R^1$.

This acylation may be carried out by the same techniques described above for the reaction depicted in equation (1). The acylation reaction (2) is also described in applicant's U.S. Ser. No. 148,139, filed May 28, 1971. The reaction between the N-haloalkanoylphoshoroamidothionate (VI) and the alkylating agent may be done according to the procedures described in U.S. Pat. No. 3,309,266 for reaction of an O,O-dialkylphosphoroamidothioate with an alkylating agent.

Suitable alkylating agents represented by $R^{1\oplus}$ include alkyl, alkenyl, and alkynyl halides, particularly iodides, e.g., methyl iodide, ethyl iodide, alkyl iodide, propargyl iodide, butyl iodide, etc., and dialkyl and dialkenyl sulfates, e.g., dimethyl sulfate, diethyl sulfate, diallyl sulfate and dihexyl sulfate.

Alternatively, the O,O-dihydrocarbyl-N-acylphosphoroamidothioate (VI) can be converted to the O,S-dihydrocarbylphosphoroamidothioate (VII) by treating the O,O-compound (VI) with a sodium alkyl mercaptide (VIII) to form the S-sodium salt and alkylating the S-sodium salt to form the O,S-compound (VII). This reaction scheme is represented by the following equations:

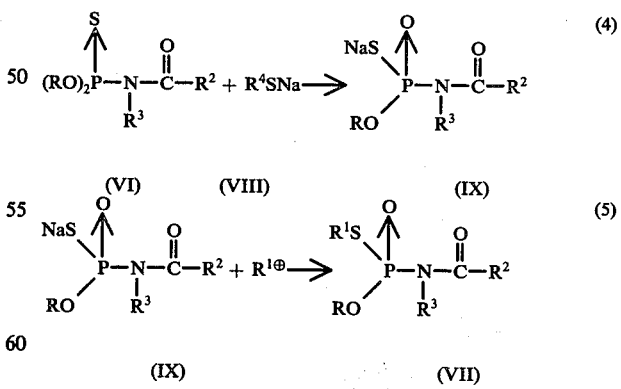

wherein $R^4$ is alkyl.

The metalation reaction depicted in equation (4) is conducted by contacting substantially equimolar amounts of the reactants (VI) and (VIII) in the liquid phase in an inert solvent at a temperature of 10°–100° C. The reaction is complete within 10 hours, more usually in 5 hours or less. The sodium salt product (IX) may be used for further reaction without separation.

The alkylation of the sodium salt (IX) is effected by mixing substantially equimolar amounts of sodium salt (IX) and the alkylating agent $R^{1\oplus}$ in an inert solvent at a temperature of in the range of 0°–80° C, preferably 25°–60° C. The product (VII) is isolated by conventional methods, e.g., extraction, chromatography, etc.

The phosphoroamidothioate compounds may also be prepared by amidating an appropriate O,O-dihydrocarbylphosphorothiochloridate to obtain an O,O-dihydrocarbyl-N-haloalkanoylphosphoroamidothioate and isomerizing said N-haloalkanoylphosphoroamidothioate with an alkylating agent as described above. This reaction scheme is illustrated by the following set of equations:

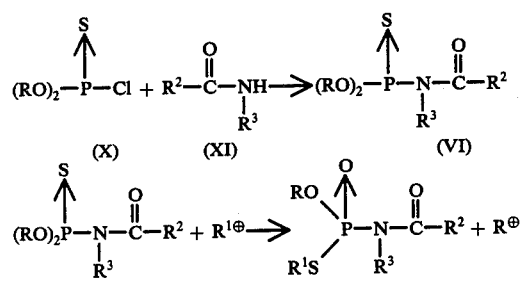

The S-hydrocarbyl-S-hydrocarbylphosphoroamidodithioate (XII) can be prepared by the reaction of phosphorous oxychloride with a mercaptan followed by amidation of the resulting S-hydrocarbyl-S-hydrocarbylphosphoroamidodithioate. The first step of the synthesis involves the addition of 2 moles of a mercaptan to 1 mole of phosphorous oxychloride ($POCl_3$) according to the following equations (if R and $R^1$ are the same, a single reaction can be carried out):

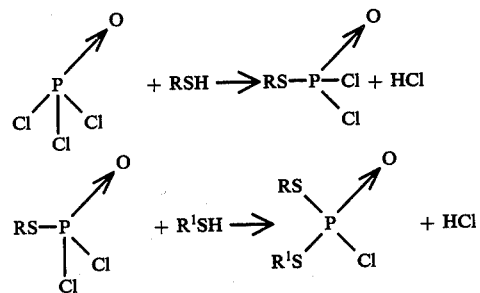

The above reactions are preferably carried out in the presence of a weak base, such as the organic amines, for example pyridine, dimethylaniline, triethylamine, etc. The base is preferably present in an amount at least equal to the moles of mercaptan. An inert organic solvent, such as diethyl ether, tetrahydrofuran, dioxane, dichloromethane, etc., may be present. The reaction temperatures are generally in the range of 0° to 15° C., preferably 0° to 5° C. The reaction time necessary to complete the addition of the mercaptan to the phosphorous oxychloride will range from about 1 to 10 hours. The S-hydrocarbyl-S-hydrocarbylphosphorochloridodithioate product can be purified by distillation, crystallization or chromatography, if desired.

The second step of the preparation, i.e., amidation, is carried out by adding gaseous ammonia or an amine to a solution of the S-hydrocarbyl-S-hydrocarbylphosphorochloridodithioate according to the following equation:

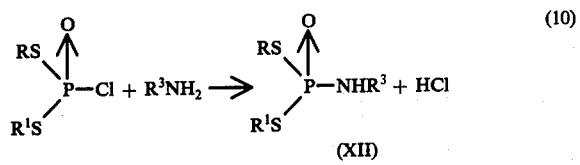

wherein R, $R^1$ and $R^3$ have the same significance as previously defined.

The reaction is preferably carried out in an inert organic solvent, such as benzene, toluene, xylene and the like, at temperatures in the range of 10° to 75° C., preferably 40° to 60° C. Completion of the reaction is indicated by cessation of ammonium chloride precipitation. Following the reaction, the crude product can be isolated by filtration and then separated from ammonium chloride by selective extraction with a solvent, such as acetone, methanol or similar organic materials.

The O,O-dihydrocarbylphoshoroamidothioate compounds used to prepared the compounds of the invention are prepared by the following reactions:

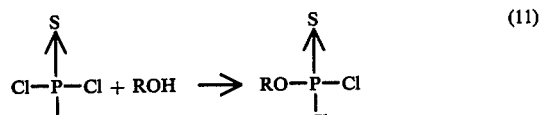

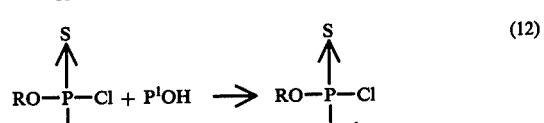

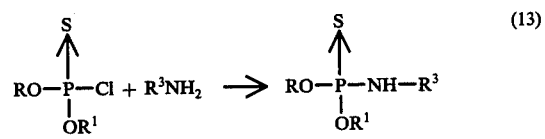

The above reactions 11–13 are conducted by essentially the same procedures described for reactions 8–10.

EXAMPLES

The following examples describe methods which may be used to prepare the phosphoroamidothioates and phosphoroamidodithioates of this invention.

EXAMPLE I

Preparation of O,S-dimethyl-N-dichloroacetylphosphoroamidothioate.

This compound was prepared by isomerizing O,O-dimethyl-N-dichloroacetylphosphoroamidothioate with dimethylsulfate according to a procedure similar to that described in U.S. Pat. No. 3,309,266. Elemental analysis on the compound is tabulated in Table I.

EXAMPLE II

Preparation of O,S-dimethyl-N-chlorobutyrylphosphoroamidothioate.

This compound was prepared by the reaction of O,S-dimethylphosphoroamidothioate (14.1g) and 4-chlorobutyryl chloride (17.1g) in methylene dichloride. Element analysis on the product is tabulated in Table I.

EXAMPLE III

Preparation of O,S-dimethyl-N-11-bromoundecanoylphosphoroamidothioate.

This compound was prepared by the reaction of O,S-dimethylphosphoroamidothioate (14g) and 11-bromoundecanoyl chloride (28.3g) in methylene dichloride (60 ml) for 3 hours at reflux temperature. Elemental analysis on the product is tabulated in Table I.

EXAMPLE IV

Preparation of O,S-dimethyl-N-chloroacetylphosphoroamidothioate.

A mixture of 40 g O,S-dimethylphosphoroamidothioates, 32 g chloroacetyl chloride and 110 ml methylene dichloride was heated at reflux for 4 hours. The reaction mixture was evaporated under reduced pressure to give the product. Elemental analysis on the product is tabulated in Table I.

EXAMPLE V

Preparation of O,S-dimethyl-N-bromoacetylphosphoroamidothioate.

This compound was prepared by the reaction of O,S-dimethylphosphoroamidothioate and bromoacetyl chloride in methylene chloride by a procedure similar to that of Example IV. The product was purified by chromatography or silica (methylene dichloride/acetone eluants). Elemental analysis on the product is tabulated in Table I.

EXAMPLE VI

Preparation of S,S-dimethyl-N-acetylphosphoroamidodithioate.

A solution of 73.2 g (0.48 mole) of phosphorous oxychloride in 300 ml of dry diethyl ether was charged to a 1 liter flask at a temperature of 0° C. A solution of 76.2 g (0.96 mole) of at and 49 g. (1.0 mole) of methyl mercaptan in 400 ml. of diethyl ether was added slowly to the flask containing phosphorous oxychloride over a 2-hour S,S-dimethylphosphoroamidodithioate. of time, maintaining the temperature from 0° to 5° C. The mixture was then stirred for an additional 6 hours at temperatures of 0° to 10° C. After 18 hours of standing at 0° C. the crude reaction product was separated from the solid residue, stripped of solvent and purified to give 31.7 g of a liquid S,S-dimethylphosphorochloridodithioate The above S,S-dimethylphosphorochloridodithioate was then charged with 500 ml of toluene to a 1 liter flask and ammonia gas added slowly at a temperature of 50° to 55° C. When the temperature started to drop, ammonia addition was stopped. The reaction was held at 50° C. for ½ hour and then cooled to room temperature and filtered. The filtrate was stripped of solvent under vacuum, then purified to give 6.6 g of S,S-dimethylphosphoroamidodithioate. The compound had a melting point of 103°–105° C., and the following N, S, P analysis:

|  | Calculated | Found |
|---|---|---|
| % N | 8.9 | 9.65 |
| % S | 41.0 | 38.1 |
| % P | 19.7 | 19.2 |

S,S-dimethylphosphoroamidodithioate was dissolved in 250 ml of dichloromethane and charged to a 500 ml flask. 39.3 g 90.5 mole) of acetylchloride was added. The solution was refluxed for 2 hours and stored at room temperature for 18 hours. The dichloromethane and excess acetylchloride was removed by evaporation and the product dissolved in 250 ml of dichloromethane to which was added 250 ml water containing sufficient calcium hydroxide to give a pH of 7 after thorough mixing. The organic phase was separated from the aqueous phase and the S,S-dimethyl-N-acetylphosphoroamidodithioate recovered from the organic phase as an oil (3.7 g). Analysis was as follows:

|  | Calculated | Found |
|---|---|---|
| % N | 7.03 | 6.48 |
| % S | 32.1 | 31.05 |
| % P | 15.52 | 14.08 |

EXAMPLE VII

Preparation of O-allyl-S-methyl-N-acetylphosphoroamidothioate.

A 68g (1.1 mole) sample of allyl alcohol was added dropwise to 84 g (0.5 mole) phosphorus thiochloride (PSCl₃) at 0°–10° C. The resulting reaction mixture was cooled in a DRY-ICE/acetone bath while 80 g (1 mole) of a 50% sodium hydroxide solution was added. After the addition was completed, the reaction mixture was stirred at about 25° C for 1½ hours, diluted with 200 ml water and 50 ml chloroform. The organic phase was separated, dried over magnesium sulfate, filtered and evaporated under reduced pressure. The residue was distilled to 31.3 g of O,O-diallylphosphorochloridothioate, b.p. 72°–74° C (0.15 mm Hg).

The above O,O-diallylphosphorochloridothioate (30 g) and 500 ml benzene were then charged to a flask and ammonia (10 g) in 100 ml benzene was slowly added. A heavy precipitate was formed in an exothermic reaction. The reaction was evaporated to give a cloudy white liquid. The liquid was diluted with 50 ml methylene chloride and refluxed with 10 g of ammonium hydroxide for ½ hour. The organic layer was washed with water, dried over magnesium sulfate, filtered and evaporated to give 20 g of O,O-diallylphosphoroamidothioate.

A 10 g (0.0518 mole) sample of the above O,O-diallylphosphoroamidothioate, 6 g (0.059 mole) acetic anhydride, 40 ml methylene chloride and 1 ml phosphoric acid was refluxed for 3 hours. The reaction mixture was diluted with 50 ml water and 100 ml aqueous saturated ammonium chloride solution. The aqueous solution was extracted with methylene chloride. The methylene chloride extracts were washed with aqueous ammonium chloride solution, dried over magnesium sulfate and evaporated to give 10.4 g of O,O-dially-N-acetylphosphoroamidothioate.

A mixture of 10 g (0.0425 mole) of the above O,O-diallyl-N-acetylphosphoroamidothioate, 4.3 g (0.0425 mole) sodium n-butyl mercaptide and 40 ml methanol was refluxed for 4 hours and then evaporated under reduced pressure to give the crude S-sodium-O-allyl-N-actylphosphoroamidothioate salt. The salt, 6 g dimethyl sulfate and 40 ml acetonitrile were then refluxed for 25 hours. A heavy precipitate formed. The reaction mixture was filtered and the filtrate was evaporated under reduced pressure to give 9 g of a yellow liquid residue. The residue was chromatographed on silica (hexane/methylene chloride/acetone eluants) to give the S-methyl-O-allyl-N-acetylphosphoroamidothioate product as an oil. Elemental analysis for $C_6H_{12}NO_3PS$ showed:

|  | Calculated | Found |
|---|---|---|
| % wt. P | 14.8 | 14.62 |
| % wt. S | 15.4 | 15.8 |

TABLE I

| Compound | Melting Point °C. | %P Calc. | %P Found | %S Calc. | %S Found | %Cl Calc. | %Cl Found |
|---|---|---|---|---|---|---|---|
| O,S-dimethyl-N-dichloroacetyl-phosphoroamidothioate | 129–132 | 12.28 | 12.60 | 12.71 | 13.27 | 28.1 | 27.2 |
| O,S-dimethyl-N-4-chlorobutyryl-phosphoroamidothioate | oil | 12.6 | 11.1 | — | — | 14.4 | 12.82 |
| O,S-dimethyl-N-11-bromoundecanoyl-phosphoroamidothioate | 55–57 | 7.96 | 7.77 | 8.25 | 8.28 | 20.58(Br) | 21.75 |
| O,S-dimethyl-N-chloroacetyl-phosphoroamidothioate | 113–114 | 14.02 | 14.08 | 14.78 | 13.90 | 16.3 | 16.5 |
| O,S-dimethyl-N-bromoacetyl-phosphoroamidothioate | 82–84 | 11.81 | 11.32 | — | — | 30.2(Br) | 28.68 |

UTILITY

The compounds of this invention were tested as follows to illustrate their insecticidal activity. For comparison, several O,O-dialkyl-N-acylphosphoroamidothioates were also tested. Test results are reported in Table II.

TEST PROCEDURES

Cabbage looper (*Trichoplusia ni*)

An acetone solution of the candidate toxicant containing a small amount of nonionic emulsifier was diluted with water to 500 ppm. Cabbage leaf sections were dipped in the toxicant solution and dried. The sections were then infested with cabbage looper larvae. Mortality readings were taken after 24 hours.

American Cockroach (*Periplaneta americana L.*)

A 500 ppm acetone solution of the candidate toxicant was placed in a microsprayer (atomizer). A random mixture of anesthetized male and female roaches was placed in a container and 55 mg. of the above-described acetone solution was sprayed on them. A lid was placed on the container. A mortality reading was made after 24 hours.

Houseflies (*Musca domestica L.*)

A 500 ppm acetone solution of the candidate toxicant was placed in a microsprayer (atomizer). A random mixture of anesthetized male and female flies was placed in a container and 55 mg. of the above-described acetone solution was sprayed on them. A lid was placed on the container. A mortality reading was made after 24 hours.

Two-spotted Mites (*Tetramuchus urticae*)

An acetone solution of the candidate toxicant containing a small amount of nonionic emulsifier was diluted with water to 100 ppm. Pinto bean leaves which were infested with mites were dipped in the toxicant solution. Mortality readings were taken after 24 hours.

Aphids (*Aphis gossypii Glover*)

An acetone solution of the candidate toxicant containing a small amount of nonionic emulsifier was diluted with water to 30 ppm. Cucumber leaves infested with the cotton aphids were dipped in the toxicant solution. Mortality readings were then taken after 24 hours.

TABLE II

| COMPOUND | % MORTALITY Cabbage Looper | Cockroach | Housefly | Mite | Aphid |
|---|---|---|---|---|---|
| O,S-dimethyl-N-dichloroacetyl-phosphoroamidothioate | 25 | 57 | 98 | 100 | 95 |
| O,S-dimethyl-N-4-chlorobutyryl-phosphoroamidothioate | 70 | 100 | 100 | 96 (30 ppm) | 96 |
| O,S-dimethyl-N-11-bromoundecanoyl-phosphoroamidothioate | 74 | 100 | 100 | 99 | 0 |
| O,S-dimethyl-N-chloroacetyl-phosphoroamidothioate | 90 | 90 | 100 | 99 | 98 |
| O,S-dimethyl-N-bromoacetyl-phosphoroamidothioate | 64 | 22 | 100 | 78 | 39 |
| S,S-dimethyl-N-acetyl-phosphoroamidodithioate | 0 | 60 | 100 | 97 | 98 |
| O-allyl-S-methyl-N-acetyl-phosphoroamidothioate | 90 | 100 | 100 | 85 (40 ppm) | 90 |
| O,O-diethyl-N-trichloroacetyl-phosphoroamidothioate | 0 | 0 | 0 | 0 | 0 |
| O,O-dimethyl-N-dichloroacetyl-phosphoroamidothioate | 0 | 0 | 99 | 0 | 0 |
| O,O-dimethyl-N-acetyl-phosphoroamidothioate | 0 | 6 | 30 | 0 | 0 |
| O,O-dimethyl-N-propionyl-phosphoroamidothioate | 0 | 0 | 2 | 0 | 0 |
| O,O-dimethyl-N-decanoyl-phosphoroamidothioate | 0 | 0 | 0 | 0 | 0 |
| O,O-dimethyl-N-crotonyl-phosphoroamidothioate | 0 | 0 | 0 | 2 | 0 |
| O,O-dimethyl-N-cyclopropyl-phosphoroamidothioate | 0 | 0 | 0 | 0 | 0 |

In addition to the specific formulations and application techniques described above, one or more of the compounds of this invention may be applied in other liquid or solid formulations to the insects, their environment or hosts susceptible to insect attack. For example, they may be sprayed or otherwise applied directly to plants or soil so as to effect control of insects coming into contact therewith.

Formulations of the compounds of this invention will comprise a toxic amount of one or more phosphoroamidothiote and/or phosphoroamidothioate and a biologically inert carrier. Usually they will also contain a wetting agent. Solid carriers such as silica, clay, talc, sawdust and the like may be used in such formulations. Liquid diluents which may be used with these compounds include water and aromatic solvents. In addition these formulations may contain other compatible pesticides, plant growth regulators, fillers, stabilizers, attractants and the like.

The term "insecticide" and "insect" as used herein refer to their broad and commonly understood usage rather than to those creatures which in the strict biological sense are classified as insects. Thus, the term "insect" is used not only to include small invertebrate animals belonging to the class *Insecta* but also to other related classes of arthropods whose members are segmented invertebrates having more or fewer than six legs, such as spiders, mites, ticks, centipedes, worms and the like.

As will be evident to those skilled in the art, various modifications on this invention can be made or followed, in the light of the foregoing disclosure and discussion, without departing from the spirit or scope of the disclosure or from the scope of the following claims.

I claim:

1. A method for killing insects which comprises applying to said insects an insecticidal amount of the compound of the formula

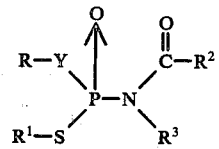

wherein R and $R^1$ individually are alkyl, alkenyl or alkynyl of up to 6 carbon atoms and $R^2$ is haloalkyl of 1 to 18 carbon atoms and of 1 to 4 fluorine, chlorine or bromine atoms, $R^3$ is hydrogen or alkyl of 1 to carbon atoms and Y is oxygen or sulfur.

2. The method of claim 1 wherein R and $R^1$ are alkyl of 1 to 3 carbon atoms, $R^2$ is haloalkyl of 1 to 3 carbon atoms and 1 to 2 fluorine, chlorine or bromine atoms, $R^3$ is hydrogen and Y is oxygen.

3. The method of claim 2 wherein R and $R^1$ are methyl.

4. The method of claim 1 wherein $R^2$ is haloalkyl of 1 to 11 carbon atoms and of 1 to 2 chlorine or bromine atoms, $R^3$ is hydrogen and Y is oxygen.

5. The method of claim 4 wherein $R^2$ is halomethyl of 1 to 2 chlorine or bromine atoms.

6. The method of claim 5 wherein R and $R^1$ are methyl.

7. The method of claim 6 wherein $R^2$ is chloromethyl, bromomethyl or dichloromethyl.

8. The method of claim 4 wherein $R^2$ is 3-chloropropyl or 10-bromodecyl and R and $R^1$ are methyl.

9. An insecticidal composition comprising an insecticidal amount of the compound defined in claim 1 and a biologically inert carrier therefor.

10. The composition of claim 9 wherein R and $R^1$ are alkyl of 1 to 3 carbon atoms, $R^2$ is haloalkyl of 1 to 3 carbon atoms and 1 to 2 fluorine, chlorine or bromine atoms, $R^3$ is hydrogen, and Y is oxgyen.

11. The composition of claim 10 wherein R and $R^1$ are methyl.

12. The composition of claim 11 wherein $R^2$ is haloalkyl of 1 to 11 carbon atoms and of 1 to 2 chlorine or bromine atoms and Y is oxygen.

13. The composition of claim 12 wherein $R^2$ is halomethyl of 1 to 2 chlorine or bromine atoms.

14. The composition of claim 13 wherein R and $R^1$ are methyl.

15. The composition of claim 14 wherein $R^2$ is chloromethyl, bromomethyl or dichloromethyl.

16. The composition of claim 12 wherein $R^2$ is 3-chloropropyl or 10-bromodecyl and R and $R^1$ are methyl.

* * * * *

UNITED STATES PATENT AND TRADEMARK OFFICE
CERTIFICATE OF CORRECTION

PATENT NO. : 4,110,443

DATED : August 29, 1978

INVENTOR(S) : Philip S. Magee

It is certified that error appears in the above-identified patent and that said Letters Patent are hereby corrected as shown below:

Abstract, line 2, "dihydrocarbylphosphoroamidothioates" should read --dihydrocarbylphosphoroamidodithioates--.

Column 4, line 5, "alkylating" should read --acylating--.

Column 7, line 38, "of at" should read --of pyridine--.

Column 7, line 41, "2-hour, S,S-Dimethylphosphoroamidodithioate" should read --2-hour period--.

Colum 8, line 54, "dially" should read --diallyl--.

Column 8, line 61, "actylphosphoroamidothioate" should read --acetylphosphoroamidothioate--.

Column 11, lines 14-15, "phosphoroamidothiote and/or phosphoroamidothioate" should read --phosphoroamidothioate and/or phosphoroamidodithioate--.

Signed and Sealed this

Sixteenth Day of October 1979

[SEAL]

Attest:

RUTH C. MASON
Attesting Officer

LUTRELLE F. PARKER
Acting Commissioner of Patents and Trademarks